(12) United States Patent
Cermak et al.

(10) Patent No.: US 6,368,280 B1
(45) Date of Patent: Apr. 9, 2002

(54) ENDOCAVITY NEEDLE GUIDE APPARATUS AND METHOD

(75) Inventors: Craig Cermak, Riverside; Brett Severence, Iowa City, both of IA (US)

(73) Assignee: CIVCO Medical Instruments Inc., Kalona, IA (US)

( * ) Notice: Subject to any disclaimer, the term of this patent is extended or adjusted under 35 U.S.C. 154(b) by 0 days.

(21) Appl. No.: 09/303,823

(22) Filed: Apr. 30, 1999

(51) Int. Cl.7 .................................................. A61B 8/14
(52) U.S. Cl. ...................................................... 600/459
(58) Field of Search ................................ 600/437, 459, 600/461, 462, 464, 466, 441; 606/96, 130; 604/116, 117

(56) References Cited

U.S. PATENT DOCUMENTS

| | | | |
|---|---|---|---|
| 4,469,106 A | * | 9/1984 | Harui .......................... 600/437 |
| 4,742,829 A | * | 5/1988 | Law et al. ................... 600/437 |
| 4,877,033 A | * | 10/1989 | Seitz, Jr. ...................... 600/441 |
| 5,052,396 A | * | 10/1991 | Wedel et al. ................ 600/461 |
| 5,076,279 A | | 12/1991 | Arenson et al. |
| 5,235,987 A | | 8/1993 | Wolfe |
| 5,469,853 A | * | 11/1995 | Law et al. ................... 600/462 |
| 5,623,931 A | | 4/1997 | Wung et al. |
| 5,758,650 A | * | 6/1998 | Miller et al. ................ 600/461 |

* cited by examiner

Primary Examiner—Marvin M. Lateef
Assistant Examiner—Ali M. Imam
(74) Attorney, Agent, or Firm—Merchant & Gould P.C.

(57) ABSTRACT

A needle guide for use in imaging analysis of cavities within the body of a human or animal. The needle guide is configured to provide a low-profile attachment to the exterior of an imaging instrument, or to be integrally formed with an imaging instrument. The needle guide includes a slot configured to receive a needle shaft, the slot having an interior surface configured to retain the needle's shaft.

18 Claims, 6 Drawing Sheets

ENDOCAVITY NEEDLE GUIDE APPARATUS AND METHOD

FIELD OF THE INVENTION

The present invention relates to a needle guide for a medical imaging instrument. More particularly, the invention is directed to an apparatus and method for guiding needles into selected locations of a patient relative to a medical instrument imaging sensor. The needle guide facilitates entry of a needle into a human or animal body.

BACKGROUND

Imaging instruments, such as ultrasound probes, have revolutionized the manner in which many important medical procedures are performed. These medical instruments utilize substantially non-invasive imaging techniques to explore and assess the condition of human tissue. As a result of these non-invasive imaging techniques, diagnostic and therapeutic protocol's have been developed that allow many highly successful and safe procedures to be performed with a minimum of disturbance to patients.

Ultrasound and other imaging techniques have received widespread acceptance as a useful diagnostic tool. Ultrasound is particularly well suited for obstetrics, where real-time scanners create a continuous image of a moving fetus that can be displayed on a monitoring screen. The image is created by emission of very high frequency sound waves from a transducer placed in contact with the mother's skin. Repeated arrays of ultrasonic beams scan the fetus and are reflected back to the transducer, where the beams are received and the data transmitted to a processing device. The processing device analyzes the information and composes a picture for display on the monitoring screen. Relative measurements may be made, and the gestational age, size and growth of the fetus can be determined. In some circumstances, a needle is guided into amniotic fluid in order to retrieve a fluid sample for analysis. These samples can be useful for diagnosing irregular conditions and can indicate that prenatal care is necessary for the fetus. Ultrasound probes, and other imaging instruments, are also used for a variety of other purposes, such as identifying the existence, location, and size of tumors, as well as the existence of other medical conditions, including the atrophy or hypertrophy of bodily organs.

Increasingly, imaging instruments have been used to explore cavities of humans and animals in order to conduct routine examinations, as well as to identify evidence of illness. These endocavities, such as those associated with the human digestive and reproductive tracts, can be the location of benign and malignant tumors. Using ultrasound, these tumors can be located and assessed. It is frequently desirable and even essential that biopsy samples of the tissue or fluid of a suspected tumor be removed for analysis. Biopsy samples may be taken by carefully directing a hand-held needle, such as a biopsy instrument, catheter, or other thin instrument (hereafter generalized as "needle" or "needles") into the body of a patient in order to remove a tissue sample. It is normally desirable that the needle be guided to a specific position within the body. Unfortunately, such hand-held direction of a needle is often inadequate—being both inaccurate and time consuming.

Various guide devices have been designed for assisting in directing needles during imaging analysis. Unfortunately, most of these devices are ill-suited for use in an endocavity. For example, U.S. Pat. Nos. 5,623,931 to Wung and 5,076,279 to Arenson are directed to needle guides for use with ultrasound imaging systems. However, neither of these needle guides is readily adaptable for insertion into an endocavity. Certain efforts have been made to devise a needle guide for insertion into endocavities, but these efforts have been of rather limited success. For example, U.S. Pat. No. 4,911,173 to Terwilliger describes a biopsy attachment for an ultrasound probe, but this biopsy attachment is complicated and cumbersome to use. Similarly, U.S. Pat. No. 5,235,987 to Wolfe teaches a needle guide for use with an imaging probe, but the needle guide does not permit the easy removal of the needle from the probe while the probe is still within the patient, nor does it allow different size needles to be used with the same needle guide.

Another specific problem with many current needle guide systems is that they are not well suited to use with a sterile cover, such as a latex film, placed over the imaging instrument. Such covers are increasingly desirable in order to maintain the ultrasound sensor in a sterile environment. The covers reduce the likelihood of contamination between patients and reduce the cost of medical procedures by minimizing sterilization costs. One challenge of working with latex and similar polymer based covers is that they have a high coefficient of friction and are subject to binding when in contact with moving pieces of an imaging sensor or needle guide. Such binding can lead to tears or punctures of the cover. For example, some prior art imaging sensors have removable pieces that are frictionally fit over a latex cover. Such designs are problematic because they can be difficult to fit and remove, as well as cause problems with binding and an ensuing risk of tearing.

Consequently, a need exists for an improved needle guide system that will allow a needle to be easily inserted and removed from a patient undergoing imaging analysis of a bodily cavity, with a minimum of discomfort to the patient. Such needle guide system should allow the needle to easily and effectively obtain a biopsy sample from a precise location within a patient. It is further desirable that the needle guide system permit the use of a sterile cover over the imaging instrument in order to reduce sterilization costs, as well as to improve hygiene.

SUMMARY OF THE INVENTION

The present invention is directed to a needle guide system for use in guiding a needle or other instrument into a patient who is undergoing imaging analysis. In specific implementations of the invention, the needle guide includes a body configured for insertion into a cavity, a slot in the body configured to receive a needle shaft, and a retaining member configured and arranged to secure the needle within the slot. The retainer member is optionally designed to be removably placed within the slot. In a particular implementation, the slot in the body has an exit for the needle, the exit configured and arranged proximate a sensor of an imaging instrument when the needle guide system is secured to the imaging instrument.

The body of the needle guide optionally has a first surface configured for securing to an imaging instrument, the first surface substantially in contact with the imaging instrument when in use. A second surface of the needle guide is exposed to the cavity and is substantially smooth and free of obstructions.

In addition, the retainer member is configured and arranged in certain implementations to be rotated within the slot such that the retainer member may assume a first position in which a needle may be removed or inserted into the slot; and a second position in which the needle is secured within the slot. Alternatively, the retainer member is configured and arranged to slide along the slot in the body, wherein an interior cross-sectional area of the slot changes as the retainer member slides along the slot in the body. In this manner, the interior cross-sectional area is changeable to accommodate needle shafts of different diameters.

In certain implementations, the body is integrally formed to an imaging instrument. Alternatively, the body is configured and arranged to be removably secured to an imaging instrument. Also, the body may be constructed for insertion over a sterile barrier. The body may include an exterior surface conforming substantially to the profile of the imaging instrument. The slot within the body may be curved to direct the end of a flexible needle or other instrument into the imaging field of an imaging instrument.

The needle guide allows the release of the needle in a manner that the needle guide and imaging instrument may be removed from the patient without removal of the needle. Such implementations are useful, for example, to drain portions of tumors, cysts, etc. within a human or animal body.

The present invention is further directed to a method for securing and directing a needle or other instrument during imaging analysis. The method includes providing a needle and a needle guide. The needle guide has a body configured for insertion into a cavity, a slot in the body configured to receive a needle shaft, and a retaining member configured and arranged to secure the needle within the slot. The needle is inserted into the needle guide, and at least a portion of the needle guide is inserted into a cavity of a patient. In specific implementations of the method, the needle guide further includes a slot in the body comprising an exit for the needle, the exit configured and arranged proximate a sensor of an imaging instrument when the needle guide system is secured to the imaging instrument. Also, the retainer member of the method may be configured and arranged to be rotated within the slot such that the retainer member may assume a first position in which a needle may be removed or inserted into the slot, and a second position in which the needle is secured within the slot.

As used herein, the term "needle" includes various long thin medical instruments, including various probes, sampling devices, and therapeutic instruments.

The above summary of the present invention is not intended to describe each discussed embodiment of the present invention. This is the purpose of the figures and the detailed description which follow.

BRIEF DESCRIPTION OF THE DRAWINGS

Other aspects and advantages of the invention will become apparent upon reading the following detailed description and references to the drawings, in which.

While the invention is susceptible to various modifications and alternative forms, specifics thereof have been shown by way of example and drawings, and will be described in detail. It should be understood, however, that the intention is not to limit the invention to particular embodiments described. On the contrary, the intention is to cover modifications, equivalents, and alternatives falling within the spirit and scope of the invention as defined by the appended claims.

DETAILED DESCRIPTION

Figure 1:
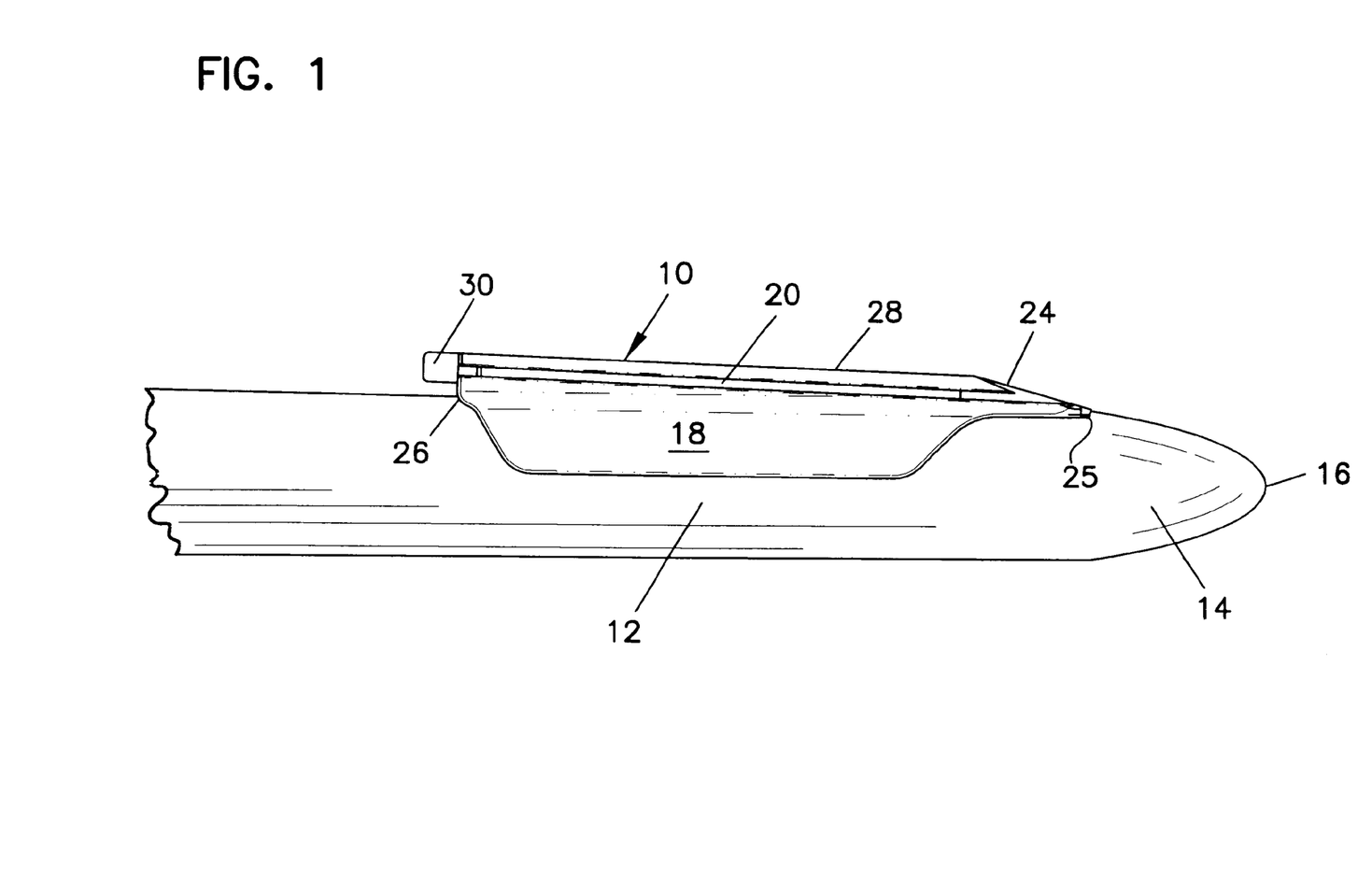
FIG. 1 is a side elevational view of a needle guide constructed and arranged in accordance with the present invention, the needle guide shown attached to the exterior of an imaging probe.
Figure 2:
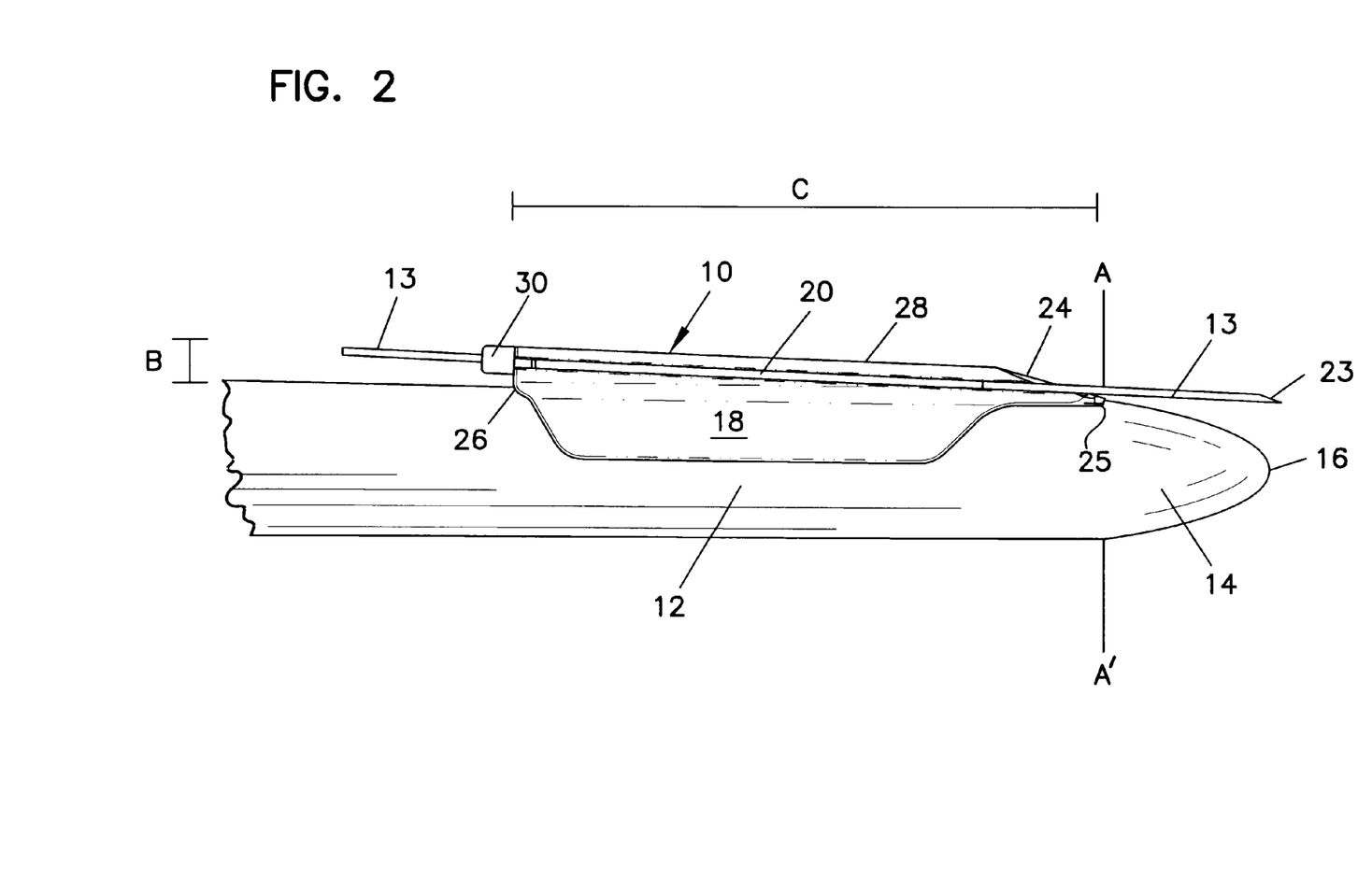
FIG. 2 is a side elevational view of the needle guide shown in FIG. 1, further showing a needle inserted into the needle guide and depicting the plane of the imaging probe as cross sectional line A–A'.
Figure 3:
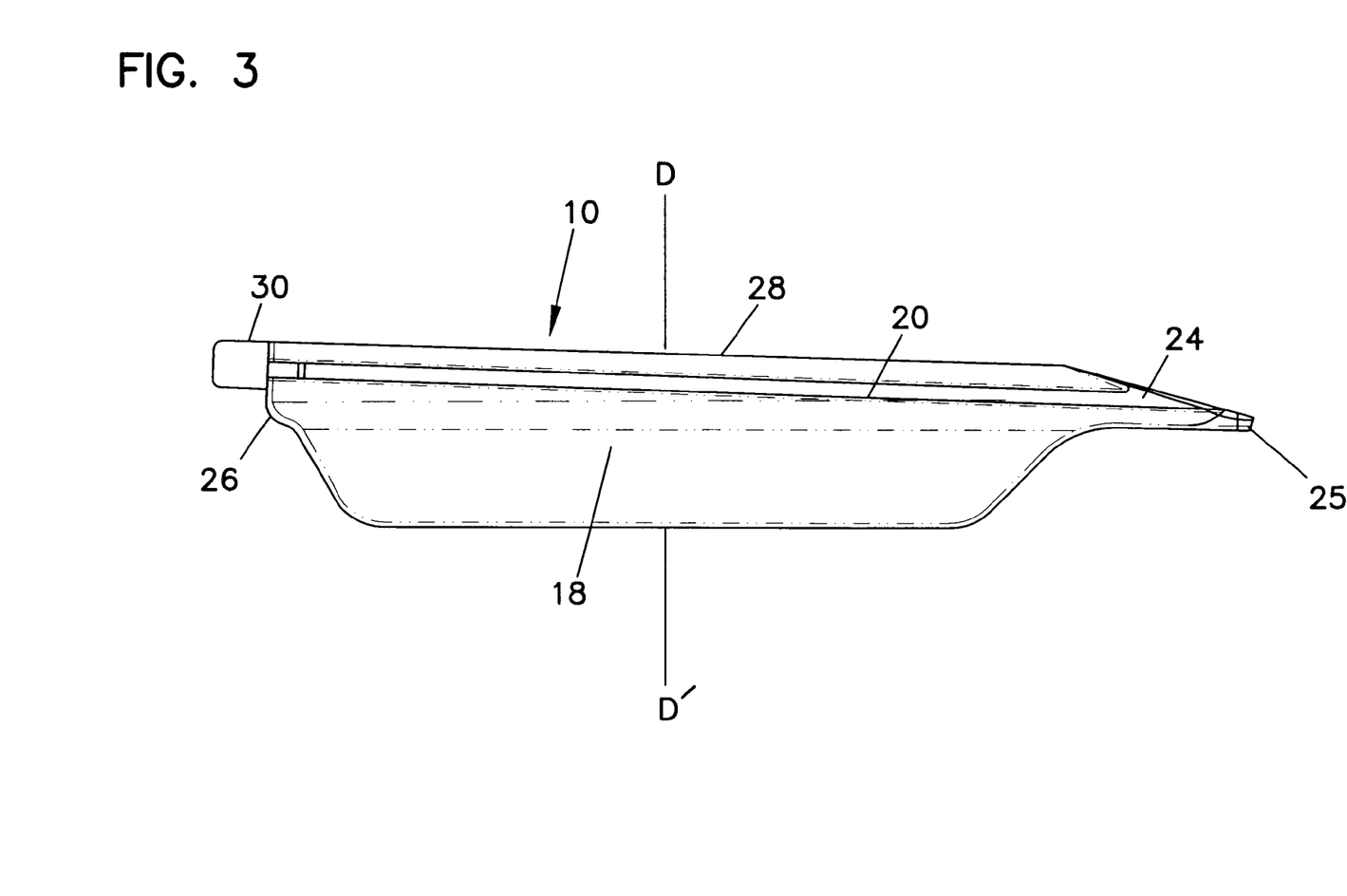
FIG. 3 is a side elevational view of a needle guide constructed and arranged in accordance with the present invention, the needle guide shown removed from an imaging probe.
Figure 4:
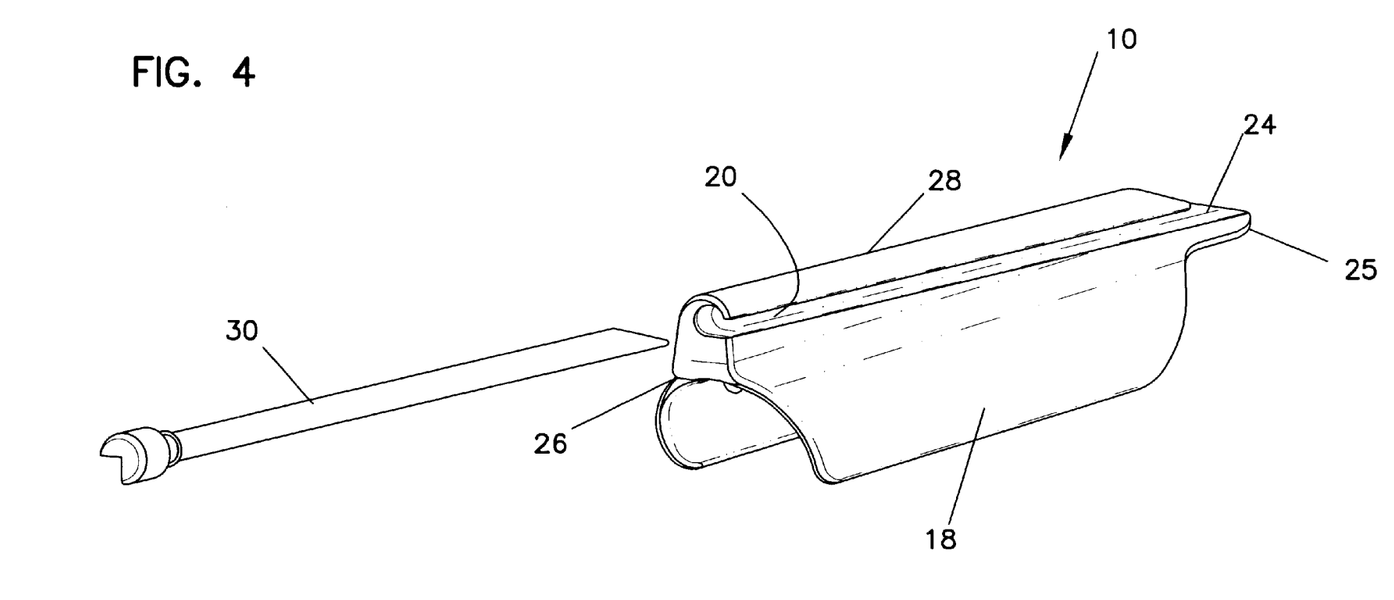
FIG. 4 is a perspective view of a needle guide constructed and arranged according to the present invention, showing a needle retainer member removed from the body of the needle guide.

The present invention is directed to a needle guide system for use in guiding a needle into a patient who is undergoing imaging analysis. Referring now to the figures, FIG. 1 shows a side elevational view of a needle guide 10 constructed and arranged in accordance with the present invention, depicting the needle guide 10 mounted on imaging probe 12. FIG. 2 shows a side elevational view of the needle guide 10 shown in FIG. 1, further showing a needle 13 inserted into the needle guide 10 and depicting the plane of the imaging probe as cross sectional line A–A'. The needle guide 10 without the imaging probe 12 is depicted in FIG. 3. Similarly, the needle guide 10 without the imaging probe 12 is shown in an exploded perspective view in FIG. 4.

The needle guide 10 is shown attached to the exterior of imaging probe 12 in FIGS. 1 and 2. The imaging probe 12 is, for example, an ultrasound probe suitable for insertion into a bodily cavity of a human or animal patient. Suitable bodily cavities include, for example, the rectum, vagina, or esophagus. As indicated in the implementation shown in FIG. 1, the imaging probe 12 used with the needle guide 10 has a generally stream-lined profile, including a sensor 14 arranged at a front end 16 of the imaging probe 12.

The depicted implementation of the needle guide 10 includes a body 18 configured for insertion into a cavity. As shown in FIGS. 1, 2, 3, and 4, a slot 20 in the body 18 is configured to receive a needle 13 (shown in FIG. 2). A retaining member 30 is configured and arranged to secure the needle 13 within the slot 20. In a particular implementation, the slot 20 in the body has an anterior exit 24 for the needle 13. The anterior exit 24 is configured and arranged proximate the sensor 14 of the imaging instrument 12 when the needle guide 10 is secured to the imaging instrument 12.

FIG. 2 depicts an observation plane of the imaging probe as A–A', which corresponds approximately to the field of view of the imaging instrument 12. Thus, the area in front of the plane defined in cross section along line A–A' is visible with the imaging instrument 12. Likewise, the area behind the plane defined along line A–A' is not visible. The needle guide 10 is configured and arranged, in specific implementations of the invention, to direct end 23 of the needle 13 into a target in the area in front of the visible plane along line A–A'

The body 18 of the needle guide 10 is constructed in a manner such that it allows the easy insertion of the needle guide 10 into the cavity of a patient, as well as the easy removal of the needle guide 10 from a patient. As is indicated in FIG. 1, the body 18 includes an anterior end 25, and a posterior end 26. The intermediate portions of the body 18 preferably have a low profile, thus assisting in insertion and removal from a body cavity. In addition, as shown in FIGS. 1, 2, 3 and 4, the body preferably is narrowest at the anterior end 25, and widest proximate the posterior end 26. It will be appreciated that the dorsal surface 28 of the needle guide 10, corresponding to the portion of the body intermediate the ends 25, 26 in contact with the body cavity when in use, is substantially fee of protrusions. To the extent that protrusions do exist, these protrusions preferably extend along the length of the body 18 such that the cross section of the needle guide 10 shows only minor marginal changes along its length. Thus, the body 18 maintains a gradual slope from the anterior end 25 up to the posterior end 26. The average slope of the body, as measured as the height "B", which is the widest portion of the needle guide above the surface of the imaging instrument 12, over the length "C" from the anterior end 25 (shown in FIG. 2) to posterior end 26 is between 0.01 and 0.30; more preferably between 0.05 and 0.20; and yet more preferably between 0.05 and 0.10.

Continuing in reference to FIGS. 1, 2, 3 and 4, the needle 13 is held within the slot 20 of the needle guide 10 with the assistance of a retainer member 30. Retainer member 30 is shown inserted within the slot 20 in FIGS. 1, 2, and 3. Retainer member 30 is optionally constructed to be removably placed within the slot 20, and is shown removed from the slot 20 in FIG. 4. In the depicted implementation, the retainer member 30 rotates in order to lock the needle 13 within the slot 20, thereby preventing accidental release of the needle 13 from the slot, but still allowing the needle 13 to be removed when desirable.

Figure 5A:
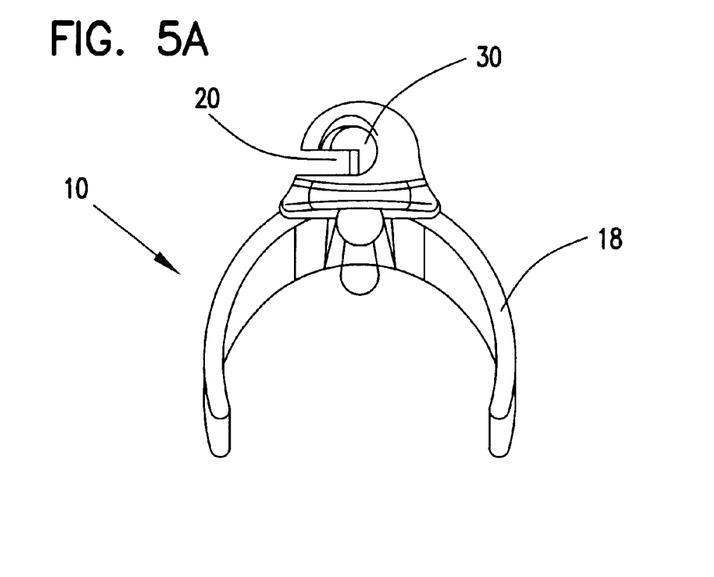
FIG. 5A is a cross-sectional view of a needle guide constructed and arranged in accordance with the present invention, taken along lines D–D' of FIG. 3, showing the needle retainer positioned in an "open" manner such that a needle can be laterally inserted into, or removed from, the needle guide.
Figure 5B:
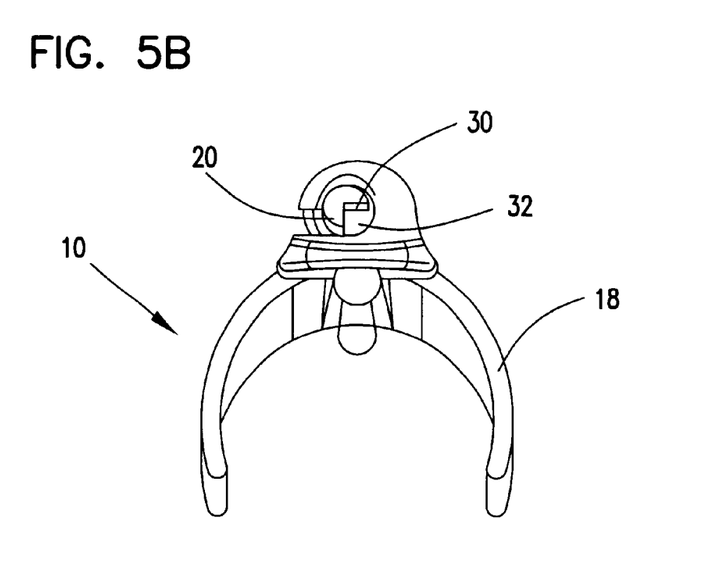
FIG. 5B is a cross-sectional view of a needle guide constructed and arranged in accordance with the present invention, showing the needle retainer positioned in a "closed" manner such that a needle is retained along its shaft within the needle guide.

The retainer member 30 is configured and arranged in certain implementations to be rotated within the slot 20 such that the retainer member 30 may assume a first position in which a needle may be removed or inserted into the slot 20; and a second position in which the needle is secured within the slot 20. The needle is typically inserted and removed form the rear of the needle guide with the retainer member closed, and is released through the slot 20 only to leave it in the body when the imaging instrument is removed from the body but the needle is desirably left within the body for a longer period of time (such as to drain a cyst). The manner in which the needle is retained within the needle guide 10 is shown more clearly in FIGS. 5A and 5B, which are cross-sectional views of the needle guide 10 taken along lines D–D' of FIG. 3. These figures show the needle guide 10 with the needle retainer 30 in an "pen" position in FIG. 5A and a "closed" position in FIG. 5B. In FIG. 5A, the needle retainer member 30 is shown such that a needle can be inserted into the slot 20 by lateral movement of the needle's shaft. In contrast, as shown in FIG 5B, the needle cannot be removed from the needle guide 10 by lateral movement of the needle shaft. However, in FIG. 5B the needle can still be removed by retracting the needle by pulling it backward. One of the advantages of this design is that it permits a needle to remain in place during and after an imaging analysis. Thus, the needle guide and imaging instrument may be removed from the body cavity without removal of the needle. Alternatively, the needle can be removed from the needle guide 10 and left within the body cavity while the imaging instrument also remains in the cavity, in which case a second needle can be inserted, if desired. As shown in the figures, it will be appreciated that the slot 20 of the needle guide 10 can be readily modified to accept needles of different diameters by incorporating retainer members 30 that have varying spaces 32 for receiving the needle guides.

Figure 6A:
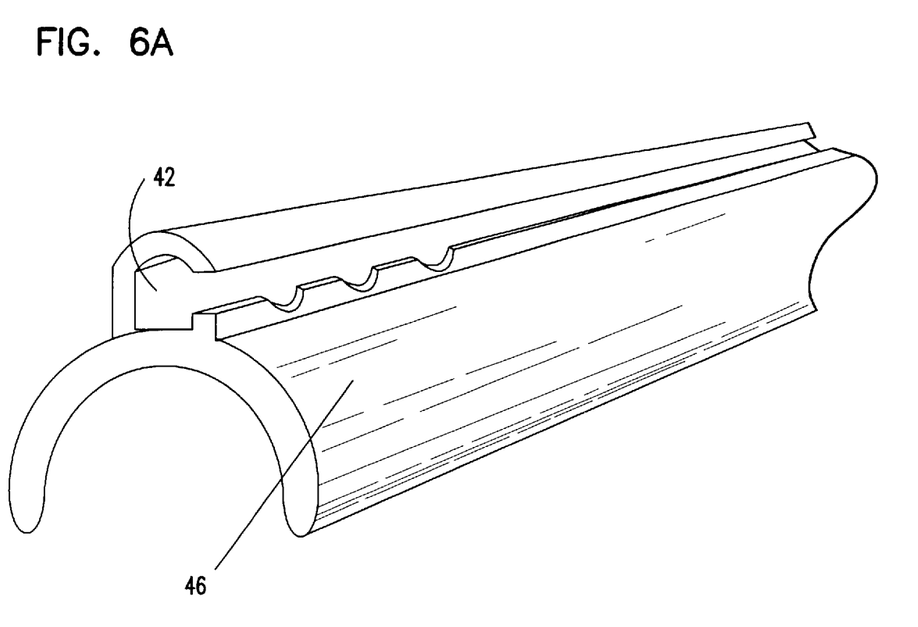
FIG. 6A is a perspective view of another implementation of a needle guide in accordance with the present invention.
Figure 6B:
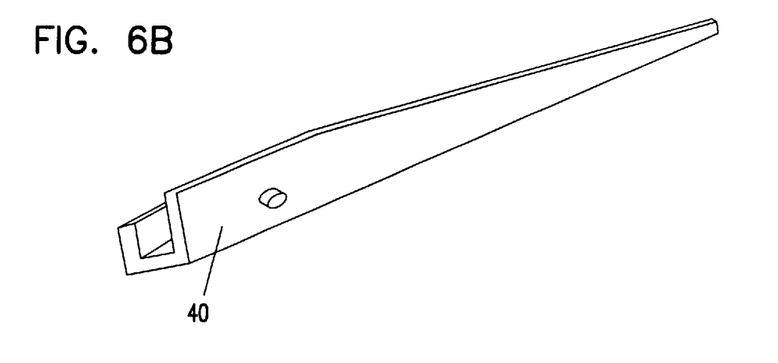
FIG. 6B is a perspective view of the needle retainer for the needle guide shown in FIG. 6A.

In another implementation of the invention, depicted in FIGS. 6A and 6B, the retainer member 40 is configured and arranged to slide along a slot 42 in the body 46, wherein the interior cross-sectional area of the slot changes as the retainer member 40 slides along the slot in the body. In this manner, the interior cross-sectional area is changeable to accommodate needle shafts of different diameters.

The body of the needle guide optionally has a first surface configured for securing to an imaging instrument, the first surface substantially in contact with the imaging instrument when in use. A second surface of the needle guide is exposed to the cavity and is substantially smooth and free of obstructions. In certain implementations, the body is integrally formed to an imaging instrument. Alternatively, the body is configured and arranged to be removably secured to an imaging instrument. Also, the body may be constructed for insertion over a sterile barrier. The body may include an exterior surface conforming substantially to the profile of the imaging instrument. The slot within the body may be curved to direct the end of a flexible needle into the imaging field of an imaging instrument. This slot may be wider than a needle shaft diameter.

The present invention is further directed to a method for retaining and directing a needle during imaging analysis. The method includes providing a needle and a needle guide. The needle guide has a body configured for insertion into a cavity, a slot in the body configured to receive a needle shaft; and a retaining member configured and arranged to secure the needle within the slot. The needle is inserted into the needle guide, and at least a portion of the needle guide is inserted into a cavity of a patient. In specific implementations of the method, the needle guide further includes a slot in the body comprising an exit for the needle, the exit configured and arranged proximate a sensor of an imaging instrument when the needle guide system is secured to the imaging instrument. Also, the retainer member of the method may be configured and arranged to be rotated within the slot such that the retainer member may assume a first position in which a needle may be removed or inserted into the slot and a second position in which the needle is secured within the slot.

The protective cover, which is normally disposable, there by prevents contamination between patients as well as provides a low-cost method of reducing sterilization requirements of the ultrasound probe and needle guide system. The needle guide is outside of the protective cover, and therefore can be disposed of after the medical procedure or sterilized using conventional methods. The protective cover is normally constructed of a thin polymer film, most often of natural or synthetic latex. While a protective cover will normally encompass the entire ultrasound probe, bracket and needle guide mounting base, it is preferred that it include an opening at a cable terminus. The cable terminus leads to the diagnostic and display equipment (not shown).

The needle guide can include a bracket for securing the needle guide to the ultrasound probe, or may optionally be integrated with the needle guide. In embodiments where a bracket is present, the bracket is configured to securely retain the mounting base and needle guide to the ultrasound probe. While the bracket may have any of numerous configurations suitable for securing mounting base and needle guide to the ultrasound probe, in at least one implementation the bracket has arms on opposite sides of the ultrasound probe. The arms fit around opposing sides of the sensor of the ultrasound probe and provide a compressive force securing the needle guide by way of the bracket to the ultrasound probe.

It will be appreciated that, although the implementation of the invention described above is directed to an ultrasound probe, the present device may be used with other medical imaging modalities, and is not limited to ultrasound probes. In addition, while the present invention has been described with reference to several particular implementations, those skilled in the art will recognize that many changes may be made hereto without departing from the spirit and scope of the present invention.

We claim:

1. A needle guide system for guiding a needle into a patient during imaging analysis, the needle guide system comprising:
    a body configured for insertion into a cavity;
    a slot in the body configured to receive a needle shaft; and
    a retaining member configured and arranged to secure the needle within the slot wherein the retainer member is configured and arranged to be removably placed within the slot; and wherein the retainer member is configured and arranged to be rotated within the slot while the body is inserted into a cavity such that the retainer member may assume:
        a first position in which a needle may be removed or inserted into the slot; and
        a second position in which the needle is secured within the slot.

2. The needle guide system according to claim 1, wherein the slot in the body further comprises an exit for the needle, the exit configured and arranged proximate a sensor of an imaging instrument when the needle guide system is secured to the imaging instrument.

3. The needle guide system according to claim 1, wherein the body comprises:
    a first surface configured for securing to an imaging instrument, the first surface substantially in contact with the imaging instrument when in use; and
    a second surface, the second surface substantially exposed to the cavity;
        wherein the second surface is substantially smooth and free of obstructions.

4. The needle guide system according to claim 1, wherein an interior cross-sectional area is changeable to accommodate needle shafts of different diameters.

5. The needle guide system according to claim 1, wherein the body is integrally formed to an imaging instrument.

6. The needle guide system according to claim 1, wherein the body is configured and arranged to be removably secured to an imaging instrument.

7. The needle guide system according to claim 6, wherein the body is configured and arranged for insertion over a sterile barrier.

8. The needle guide system according to claim 1, further comprising:
    an imaging instrument;
        wherein the body further comprises an exterior surface conforming substantially to the profile of the imaging instrument.

9. The imaging instrument according to claim 1, wherein the slot is curved to direct the end of a flexible needle into the imaging field of an imaging instrument.

10. The needle guide system according to claim 1, wherein the slot is wider than a needle shaft diameter.

11. A needle guide system for guiding a needle into a patient during imaging analysis, the needle guide system comprising:
    a body configured for insertion into a cavity and retention over a sterile barrier;
    a slot in the body configured to receive a needle shaft; and
    a retaining member configured and arranged to secure the needle within the slot;
        wherein the retainer member is configured and arranged to be removably placed within the slot and wherein the retainer member is configured and arranged to slide along the slot in the body, wherein an interior cross-sectional area of the slot changes as the retainer member slides along the slot in the body.

12. The needle guide system according to claim 11, wherein the slot in the body further comprises an exit for the needle, the exit configured and arranged proximate a sensor of an imaging instrument when the needle guide system is secured to the imaging instrument.

13. The needle guide system according to claim 11, wherein the body comprises:
    a first surface configured for securing to an imaging instrument, the first surface substantially in contact with the imaging instrument when in use; and
    a second surface, the second surface substantially exposed to the cavity;
        wherein the second surface is substantially smooth and free of obstructions.

14. The needle guide system according to claim 11, wherein the retainer member is configured and arranged to be rotated within the slot such that the retainer member may assume:
    a first position in which a needle may be removed or inserted into the slot; and
    a second position in which the needle is secured within the slot.

15. A method for retaining and directing a needle during imaging analysis, the method comprising:
    providing a needle;
    providing a needle guide comprising:
        a body configured for insertion into a cavity, a slot in the body configured to
        receive a needle shaft; and a retaining member configured and arranged to secure the needle within the slot, wherein the retainer member is configured and arranged to be removably placed within the slot; and wherein the retainer member is configured and arranged to be rotated within the slot while the body is inserted into a cavity such that the retainer member may assume:
            a first position in which a needle may be removed or inserted into the slot; and
            a second position in which the needle is secured within the slot;
    inserting the needle into the needle guide; and
    inserting at least a portion of the needle guide into a cavity of a patient.

16. The method according to claim 15, wherein the needle guide further includes a slot in the body comprising an exit for the needle, the exit configured and arranged proximate a sensor of an imaging instrument when the needle guide system is secured to the imaging instrument.

17. The method according to claim 16, wherein the retainer member is configured and arranged to be rotated within the slot such that the retainer member may assume a first position in which a needle may be removed or inserted into the slot and a second position in which the needle is secured within the slot.

18. The method according to claim 15, wherein the retainer member is configured and arranged such that the needle is slidably removable from the needle guide.

* * * * *